United States Patent [19]

Kögler et al.

[11] Patent Number: 4,772,490

[45] Date of Patent: Sep. 20, 1988

[54] METHOD FOR PRODUCING A WATER-PERMEABLE COVERING ON GRANULAR WATER-SOLUBLE SUBSTANCES

[75] Inventors: Hubert Kögler, Mettmann; Reinhard Winter; Peter Kuhlmann, both of Wülfrath, all of Fed. Rep. of Germany

[73] Assignee: Ashland Oil, Inc., Russell, Ky.

[21] Appl. No.: 942,155

[22] Filed: Dec. 16, 1986

[30] Foreign Application Priority Data

Dec. 16, 1985 [DE] Fed. Rep. of Germany ....... 3544451

[51] Int. Cl.$^4$ .................. B05D 7/00; A01N 25/00; C05G 5/06
[52] U.S. Cl. .................... 427/212; 71/64.07; 427/221
[58] Field of Search .................. 71/64.02, 64.07; 427/212, 221; 428/407, 423.1

[56] References Cited

U.S. PATENT DOCUMENTS

| | | | |
|---|---|---|---|
| 3,223,518 | 12/1965 | Hansen | 71/64.07 |
| 3,429,848 | 2/1969 | Robins | 260/38 |
| 3,432,457 | 3/1969 | Robins | 260/30.4 |
| 3,632,844 | 1/1972 | Robins | 260/18 TN |
| 3,702,316 | 11/1972 | Robins | 260/38 |
| 3,726,867 | 4/1973 | Robins | 260/30.4 N |
| 3,744,987 | 7/1973 | Omara et al. | 71/64.07 |

FOREIGN PATENT DOCUMENTS 38361 3/1977 Japan .................. 71/64.07

*Primary Examiner*—Michael R. Lusignan
*Attorney, Agent, or Firm*—Pollock, Vande Sande & Priddy

[57] ABSTRACT

The invention relates to a method for producing a water-permeable covering on granular, water-soluble substances by coating them with a synthetic resin. The method of the invention uses a coating composition which comprises a polyisocyanate and a polyol component of a condensation product from phenols and aldehydes, a softener containing hydroxyl groups and optionally a diluent containing hydroxyl groups. The coating composition is cured at room temperature with an amine as a catalyst.

30 Claims, No Drawings

METHOD FOR PRODUCING A WATER-PERMEABLE COVERING ON GRANULAR WATER-SOLUBLE SUBSTANCES

DESCRIPTION

1. Technical Field

The invention relates to a method for producing a water-permeable covering on granular, water-soluble substances by coating them with a coating composition which consists of a polyisocyanate and a polyol component and is cured with an amine as a catalyst. Due to this covering, the substance is released from the coated granules to the environment steadily over a prolonged period.

2. Background Art

The coating of granular substances, such as mineral fertilizers with synthetics to reduce the dissolution rate and to thus prolong the period over which they are effective is known for instance from NL-PS No. 129,279 and DE-AS No. 21 55 924. According to NL-PS No. 129,279, for instance linseed oil dicyclopentadiene copolymer is used for this purpose. Coating requires temperatures higher than 50° C., for instance 82° to 121° C. The coating times are from 1 to 2 hours, involving high amounts of energy and long cooling times. These methods are therefore relatively laborious and expensive. Consequently, coated mineral fertilizers have so far been utilized to a limited extent only, although they offer considerable advantages not only in view of the fact that the plants are supplied with the nutrients steadily over a prolonged period of time but also from an environmental point of view. The same applies to granular, water-soluble substances, such as drying agents, e.g. phosphorus pentoxide or calcium chloride, coated with water-permeable synthetic resins.

Moreover, the high temperatures required for obtaining the coverings according to the known methods pose great difficulties where the substances to be coated are combustibles or explosives, such as ammonium nitrate.

SUMMARY OF THE INVENTION

It is the object of the present invention to provide a method for producing a water-permeable covering on granular water-soluble substances by coating them with a synthetic resin, which can be performed at room temperature and does not require additional heating. This method is to yield coverings that are water-permeable or vapor-permeable in both directions and allow the substance dissolved from the granular material to be transported to the outside. The covering itself must not dissolve rapidly in water as the granular substance is to be prevented from being released too quickly to the environment. Nor must the covering be too brittle, but must possess a certain elastic strength required for transport and storage, as otherwise the covering would be damaged and the granular substance be released spontaneously. Finally, the method is to facilitate coating the granular material rapidly at room temperature, which presupposes rendering the covering quickly non-tacky and the covered material free flowing.

This object is achieved by the surprising finding that it is possible to obtain a water-permeable covering showing the afore-mentioned excellent properties by coating granular water-soluble substances with a coating composition of a polyisocyanate and a specific polyol component and curing the coating composition with an amine as a catalyst.

The invention therefore relates to a method for producing a water-permeable covering on granular, water-soluble substances by coating them with a synthetic resin, the method being chararacterized (a) in that the granular, water-soluble substance is covered with a coating composition which comprises a polyisocyanate and a polyol component consisting of a condensation product of phenols and aldehydes, a softening agent containing hydroxyl groups and optionally a diluting agent containing hydroxyl groups, and (b) in that the coating composition is cured with an amine as a catalyst.

BEST AND VARIOUS MODES FOR CARRYING OUT THE INVENTION

The method of the present invention is suitable to provide practically all granular, water-soluble substances with water-permeable coatings. The method of the invention can therefore be used for treating all substances which are to be released to the environment in a controlled manner over a prolonged period of time. Examples of such substances are water-soluble fertilizer granules. The method of the invention is also suitable to coat hygroscopic substances, such as drying agents, e.g. calcium chloride and phosphorus pentoxid, which are to be prevented from diluting rapidly in a vapor-containing atmosphere.

The grain size of the granular substances to be coated is not critical. It may for instance range from 0.5 to 10 mm. The medium grain size ranging from 1 to 5 mm is preferred.

The rate at which the active ingredient is being released from the granular substance covered according to the method of the invention can be adjusted by varying the polyol and isocyanate components and the thickness of the covering and its polyurethane content, with the result that in the case of fertilizer granules for instance, an effective period of from 1 month to 1 year can be achieved.

The coating according to the method of the invention is performed most easily in a rotating vessel, for instance a drum, which is preferably provided with a rim scraper. The coating composition which consists of a polyisocyanate component and a polyol component is placed continuously or step-wise onto the granular substance present in the drum.

Aliphatic, cycloaliphatic, aralphatic, aromatic and heterocyclic polyisocyanates may be used as the polyisocyanate component for preparing the polyurethane coatings of the invention. Preferred polyisocyanates are aromatic polyisocyanates having at least two isocyanate groups in the molecule. Specific examples of particularly suited aromatic polyisocyanates are diphenyl methane diisocyanate (MDI) and toluene diisocyanate (TDI). Moreover, mixtures of polyisocyanates and polyisocyanate prepolymers are also suitable.

The polyol component of the coating composition consists of a condensation product of phenols and aldehydes and of a softener containing hydroxyl groups. A diluting agent containing hydroxyl groups may be added. Consequently, all components of the polyol component bear functional groups (hydroxyl groups) which are reactive to isocyanate groups and take part in the polyurethane reaction. This is an essential aspect of the invention, as the cover thus does not have organic components that are not chemically bound, which might be released from the cover when the granular water-soluble substance is gradually removed and cause environmental problems.

The afore-mentioned numerous important properties of the cover are achieved in particular by deliberately selecting the resin components of the polyol component. In the process of the invention, condensation products of phenols and aldehydes may be used as resins. Specific examples of these are benzyl ether resins, novolaks and water-soluble resols. These resins contain at least 2, preferably 2 to 8 hydroxyl groups in the molecule. Benzyl ether resins composed of units having the formula

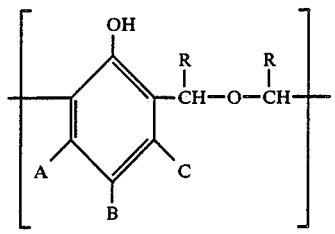

are especially preferred, wherein A, B and C are the same or different and each mean a hydrogen or halogen atom, a $C_{1-8}$ hydrocarbon or oxyhydrocarbon residue and R is a hydrogen atom or an $C_{1-8}$ hydrocarbon residue.

The condensation product of phenols and aldehydes (resin component) is contained in the polyol component in an amount of 10 to 90, preferably 20 to 70 weight %. Where the content is less than 10 weight %, no water-permeable coatings of sufficient strength are obtained, while with a resin portion higher than 90 weight %, the elasticity of the coatings becomes insufficent.

The second component of the polyol component is a softener containing hydroxyl groups. Suitable substances are those which are used in polyurethane chemistry for this purpose, with castor oil and polyether polyols yielding excellent elastic coatings possessing the desired properties.

To adjust the viscosity of the coating composition, a diluent containing hydroxyl groups may be added to the polyol component, if necessary. Here too, the substances commonly used for this purpose in polyurethane chemistry may be employed, for instance monofunctional alcohols, such as butanol or diacetone alcohol. Optionally, the polyether polyols already mentioned as softeners may also be used as diluents.

The relative amounts used of softener and diluent are not particularly critical. The amounts of the two substances and the afore-mentioned resin component make up the polyol component used according to the invention.

After application to the granular water-soluble substance to be coated, the coating composition is cured with an amine as a catalyst. In this process the amine may be used either as gaseous mixture with air or inert gas or be added in liquid state to the polyol component.

Where the catalyst-gassing technique is employed, it is preferable to use low-boiling tertiary amines, such as trimethylamine, triethylamine, dimethylethyl amine or dimethyl isopropylamine. The catalyst-gas mixture can be prepared by passing air or an inert gas through a gas washing bottle filled with amine, whereby the air or the inert gas is being enriched by or saturated with gaseous amine. In this embodiment, the favourable catalyst concentrations of the catalyst-gas mixture are between 0.1 vol. % and the saturation concentration of the used amine at room temperature.

In another embodiment of the invention the amine catalyst may also be admixed in liquid form to the polyol component. For this purpose, higher-boiling amines, such as dimethyl ethanolamine, triethanol amine or vinylimidazole may be used, apart from the above-mentioned tertiary amines.

The liquid amine is admixed to the polyol component in an amount of 0.1 to 5.0 vol %.

During coating the granular, water-soluble substance is constantly moved in order to ensure even coating. After application of the coating composition which either incorporates the catalyst or is gassed with the catalyst, the coating resin hardens in very short time forming a polyurethane film on the granular, water-soluble substance. In a short time, that is in less than 15 minutes, mostly in less 5 minutes, a non-tacky covering and free flowing coated granules can be obtained by this process. As hardening proceeds at room temperature, it is possible to also coat dangerous substances, such as ammonium nitrate, without any problems.

The coating composition is usually employed in an amount of about 3 to 40 weight %, based on the granular water-soluble substance to be coated. The rate at which the substance is being released from the coated grains essentially depends on the amount of the coating composition and, as a consequence, on the thickness of the covering.

Apart from the method described, other known coating techniques, such as fluidization coating, may also be used, where it is ensured that the granules to be coated are contacted by the coating composition and the possibly necessary catalyst gas mixture.

As is usual in polyurethane chemistry, the components of the coating composition are employed in a substantially anhydrous form. This means that the amount of residual water should be less than about 1 weight %. The polyol component may optionally also incorporate an agent for removing residual moisture, as is known in the field of polyurethanes.

The coating composition may, where desired, also contain other modifying agents, fillers, or other components which are advantageous for the particular purpose of use of specific coated granules. If the granular, water-soluble substance which is being coated is a fertilizer, the coating composition may be admixed for instance with trace elements important for plant growth or with systemic pesticides. If the granular, water-soluble substance to be coated is not used in a sector where it might be detrimental to environment, the coating compositions (e.g. the polyol component) may be admixed with further, non-reactive components, for instance softeners known from polyurethane chemistry, such as dioctylphthalate or dibutylphthalate or diluents, such as esters, ketones or hydrocarbons (aliphatic or preferably aromatic ones).

The examples illustrate the invention.

EXAMPLE 1

A commercial NPK (nitrogen, phosphorus, potassium) fertilizer having a composition of 15/15/15 and an average grain size of 3 mm is used as the basic fertilizer.

The polyol component 1 has the following composition:

60 parts of a benzylether resin prepared from 1 mole of phenol and 1.6 moles of formaldehyde, and having a hydroxyl content of 16.5% are homogeneously mixed with 36 parts of castor oil and 18 parts of diacetone alcohol at 50° C.

A technical diphenylmethanediisocyanate-based polyisocyanate having a isocyanate content of 30 to 32% is used as the isocyanate component.

A bowl rotating at about 60 rpm and equipped with scraper serves as coating equipment in which the fertilizer granules are constantly moved during coating.

Nitrogen saturated with triethylamine at 20° C. is used as the catalyst-gas mixture. This mixture is passed into the open bowl via a tube at a rate of 50 l/h.

500 g of the basic fertilizer are placed into the described equipment.

37.5 g of polyol component 1 and 37.5 g of the isocyanate component are premixed and divided into 3 approximately equal portions.

The 3 portions are charged into the rotating bowl one after the other at intervals of 1 minutes, while gassing is continued. After the last portion is added, the granules are kept moving while gassing is continued. Then they are removed from the equipment. At this time, the coating has already hardened to such a degree that the thus covered fertilizer can be stored without any problems; it does not turn lumpy nor is the covering damaged. The final hardening is achieved after 24 hours. The coating comprises 15 weight % of polyurethane, based on the fertilizer.

EXAMPLE 2

The basic fertilizer and the equiment are the same as in example 1.

The polyol component has the following composition:

30 parts of benzylether resin prepared from 1 mole of phenol and 1.2 mole of formaldehyde and having a hydroxyl content of 16.9% are homogenously mixed with 60 parts of castor oil and 10 parts of diacetone alcohol at 50° C.

Nitrogen saturated with dimethylethylamine at 20° C. is used as the catalyst gas mixture.

As in example 1, 500 g of the basic fertilizer are placed into the vessel.

37.5 g of polyol component 2 and 37.5 g of isocyanate component of example 1 are premixed. The basic fertilizer is coated as in example 1 (15 weight % of polyurethane, based on the fertilizer).

EXAMPLE 3

Example 2 is repeated with 31.25 g of polyol component 2 and 31.25 g of the isocyanate component (12.5 weight % of polyurethane, based on the fertilizer).

EXAMPLE 4

Example 2 is repeated with 43.75 g of polyol component 2 and 43.75 g of the isocyanate component (17.5 weight % of polyurethane, based on the fertilizer).

EXAMPLE 5

Example 2 is repeated with the modification that 10 parts of a molecular sieve on the basis of zeolith are admixed to 100 parts of the polyol component (polyol component 3). 37.5 g of polyol component 3 and 37.5 g of isocyanate component are used (15 weight % of polyurethane, based on the fertilizer).

Determination of the release of the active ingredient:

To determine the period over which the active ingredient is being released, 12.5 g each of the coated fertilizer prepared according to examples 1 to 5 are palced into 250 g water and stored at 22° C. The dissolved active ingredient is determined by measuring the electric conductivity. The dissolved active ingredients can be calculated by a comparison with uncoated basic fertilizers.

As comparative example 6, a commercial coated fertilizer with protected activity (nitrogen phosphorus potassium 14/14/14), the period over which the fertilizer is stated to be effective being 3 to 4 months is determined at the same time under the usual soil conditions.

Amount of the dissolved active ingredient expressed in %

| time | Example | | | | | Comparison |
|---|---|---|---|---|---|---|
| | 1 | 2 | 3 | 4 | 5 | 6 |
| 1 day | 4,2 | 15,0 | 18,9 | 5,7 | 4,7 | 14,3 |
| 2 days | 14,3 | 27,6 | 32,7 | 13,0 | 10,8 | 24,1 |
| 1 week | 21,2 | 61,5 | 62,0 | 48,0 | 26,5 | 39,7 |
| 2 weeks | 30,0 | 72,2 | 75,7 | 70,0 | 45,2 | 51,2 |
| 3 weeks | 31,5 | 75,5 | 80,0 | 71,2 | 51,5 | 53,0 |
| 4 weeks | 37,5 | 79,0 | 81,5 | 76,0 | 61,5 | 59,0 |
| 5 weeks | 40,0 | 80,2 | 82,5 | 78,0 | 66,7 | 62,0 |

Coating of drying agents

EXAMPLE 7

Phosphorus pentoxide granules having an average grain size of 4 mm are used as drying agent.

500 g of the phosphorus pentoxide are placed into the vessel as described in example 1 and coated with 17.5 g of polyol component 1 and 17.5 g of the isocyanate component described in Example 1 (7 weight % of polyurethane based on phosphorus pentoxide).

Nitrogen saturated with dimethylethyl amine at 20° C. is used as the catalyst gas mixture.

EXAMPLE 8

The phosporus pentoxide described in example 7 and the coating equipment described in example 1 are used. A polyol component 4 having the following composition is used:

60 parts of a benzyl ether resin prepared from 1 mole of phenol and 1.4 moles of formaldehyde having a hydroxyl content of 16.7% are homogenously mixed at 50° C. with 5 parts of castor oil, 5 parts of dioctylphthalate, 10 parts of an aromatic hydrocarbon mixture having a boiling range of from 160° to 180° C. and 20% of diacetone alcohol. To this mixture, 2 parts of dimethyl ethanol amine are subsequently added at room temperature.

24 g of said polyol component 4 and 23,5 g of the isocyanate component are both divided into two equal portions.

500 g of phosphorus pentoxide are placed into the coating equipment and the first portion of the polyol component is added.

After about 1 minute, the first portion of the isocyanate component is added. The second polyol component follows after 5 to 6 minutes and the second portion of the isocyanate component after one further minute. The granules are kept moving for 10 more minutes. Curing is then complete and the granules are no longer tacky (9.5 weight % of polyurethane, based on phosphorus pentoxide).

We claim:

1. A method for producing a water-permeable covering on granular, water-soluble substances by coating said substances with a synthetic resin which comprises:
   (a) covering said granular, water-soluble substances with a coating composition which comprises a polyisocyanate and a polyol component that includes:
      (1) condensation product of phenols and aldehydes, and
      (2) hydroxyl group containing softener; wherein said condensation product is 10-90% by weight of said polyol component and wherein the relative amounts of said polyisocyanate and said polyol component are such as to provide a polyurethane covering upon hardening; and
   (b) hardening said coating composition employing an amine as a catalyst to provide a cured polyurethane covering.

2. The method according to claim 1, characterized in that the catalyst is used as a gaseous mixture of an amine and air or inert gas.

3. The method according to claim 1, characterized in that the catalyst is mixed in a liquid state with the polyol component.

4. The method according to claim 1, characterized in that the polyisocyanates used are aromatic polyisocyanates.

5. The method of claim 1 wherein said polyol component further includes a diluting agent that contains a hydroxyl group.

6. The method according to claim 1, characterized in that benzyl ether resins, novolaks or anhydrous resols are used as the condensaiton product of phenols and aldehydes.

7. The method according to claim 1, characterized in that castor oil or a polyether polyol is used as the hydroxyl group containing softener.

8. The method according to claim 5, characterized in that diacetone alcohol, butanol or a polyether polyol is used as the hydroxyl group-containing diluting agent.

9. The method according to claim 1, characterized in that the polyol component used contains an agent for removing residual moisture.

10. The method of claim 1 wherein said granular water-soluble substances are water-soluble fertilizer granules having an average size of 0.5 mm to 10 mm each.

11. The method of claim 10 wherein trace elements important for the growth of the plant or systemic pesticides are added to said coating composition.

12. The method of claim 1 wherein said granular water-soluble substances are water-soluble drying agents.

13. The method of claim 10 wherein said granules have an average size of 1 mm to 5 mm each.

14. The method of claim 1 wherein a polyol component is used which comprises 20 to 70 weight % condensation product of phenols and aldehydes.

15. The method of claim 2 wherein said granular water-soluble substances are water-soluble fertilizer granules having an average size of 0.5 mm to 10 mm each.

16. The method of claim 3 wherein said granular water-soluble substances are water-soluble fertilizer granules having an average size of 0.5 mm to 10 mm each.

17. The method of claim 4 wherein said granular water-soluble substances are water-soluble fertilizer granules having an average size of 0.5 mm to 10 mm each.

18. The method of claim 6 wherein said granular water-soluble substances are water-soluble fertilizer granules having an average size of 0.5 mm to 10 mm each.

19. The method of claim 7 wherein said granular water-soluble substances are water-soluble fertilizer granules having an average size of 0.5 mm to 10 mm each.

20. The method of claim 8 wherein said granular water-soluble substances are water-soluble fertilizer granules having an average size of 0.5 mm to 10 mm each.

21. The method of claim 9 wherein said granular water-soluble substances are water-soluble fertilizer granules having an average size of 0.5 mm to 10 mm each.

22. The method of claim 2 wherein said granular water-soluble substances are water-soluble drying agents.

23. The method of claim 3 wherein said granular water-soluble substances are water-soluble drying agents.

24. The method of claim 4 wherein said granular water-soluble substances are water-soluble drying agents.

25. The method of claim 6 wherein said granular water-soluble substances are water-soluble drying agents.

26. The method of claim 7 wherein said granular water-soluble substances are water-soluble drying agents.

27. The method of claim 8 wherein said granular water-soluble substances are water-soluble drying agents.

28. The method of claim 9 wherein said granular water-soluble substances are water-soluble drying agents.

29. The method of claim 1 wherein said hardening is carried out without the addition of heat.

30. The method of claim 1 wherein the amount of said coating composition is about 3 to 40 weight % based on said granular water-soluble substance.

* * * * *